(12) United States Patent
Jo et al.

(10) Patent No.: US 12,727,753 B2
(45) Date of Patent: Sep. 8, 2026

(54) HAND-HELD SCANNER

(71) Applicant: MEDIT CORP., Seoul (KR)

(72) Inventors: Eun Gil Jo, Seoul (KR); Sang Cheol Lee, Seoul (KR)

(73) Assignee: MEDIT CORP., Seoul (KR)

(*) Notice: Subject to any disclaimer, the term of this patent is extended or adjusted under 35 U.S.C. 154(b) by 238 days.

(21) Appl. No.: 18/286,915

(22) PCT Filed: Apr. 12, 2022

(86) PCT No.: PCT/KR2022/005287
§ 371 (c)(1),
(2) Date: Oct. 13, 2023

(87) PCT Pub. No.: WO2022/220547
PCT Pub. Date: Oct. 20, 2022

(65) Prior Publication Data

US 2024/0197162 A1 Jun. 20, 2024

(30) Foreign Application Priority Data

Apr. 14, 2021 (KR) ........................ 10-2021-0048819
Dec. 21, 2021 (KR) ........................ 10-2021-0184287

(51) Int. Cl.
*A61B 1/24* (2006.01)
*A61B 1/00* (2006.01)
(Continued)

(52) U.S. Cl.
CPC ............ *A61B 1/24* (2013.01); *A61B 1/00172* (2013.01); *G02B 13/0095* (2013.01);
(Continued)

(58) Field of Classification Search
CPC .. A61B 1/24; A61B 1/00172; G02B 13/0095; G02B 26/0833; G02B 26/101;
(Continued)

(56) References Cited

U.S. PATENT DOCUMENTS 6,377,409 B2 4/2002 Kanai
9,274,405 B2 3/2016 Tohara et al.
(Continued)

FOREIGN PATENT DOCUMENTS

CN 201314977 Y * 9/2009
JP 10-221511 A 8/1998
(Continued)

OTHER PUBLICATIONS

International Search Report of PCT/KR2022/005287 dated Jul. 22, 2022 [PCT/ISA/210].

(Continued)

*Primary Examiner* — Michael Lee
(74) *Attorney, Agent, or Firm* — Sughrue Mion, PLLC

(57) ABSTRACT

Provided is a hand-held scanner including: a body in a longitudinal direction; and an optical engine provided in the body and configured to output light, wherein the optical engine includes: a lighting unit configured to emit, along a first axis, light generated from at least one light source; and a projection unit configured to project light emitted from the lighting unit, along a second axis being parallel to the first axis, and wherein directions of the first axis and the second axis are equal.

11 Claims, 10 Drawing Sheets

(51) Int. Cl.
*G02B 13/00* (2006.01)
*G02B 26/08* (2006.01)
*G02B 26/10* (2006.01)
*G02B 27/28* (2006.01)

(52) U.S. Cl.
CPC ....... *G02B 26/0833* (2013.01); *G02B 26/101* (2013.01); *G02B 27/283* (2013.01)

(58) Field of Classification Search
CPC ...... G02B 27/283; G02B 27/00; G02B 27/28; G01B 11/25
See application file for complete search history.

(56) References Cited

U.S. PATENT DOCUMENTS

2005/0280779 A1 12/2005 Shimizu
2007/0019165 A1* 1/2007 Ishikura .................. G02B 5/04 348/E5.142
2009/0128784 A1* 5/2009 Yoon ...................... G03B 21/28 353/31
2012/0038819 A1* 2/2012 McMackin ........... H04N 25/00 348/E5.024
2013/0201081 A1* 8/2013 Evans ................. G02B 27/017 345/8
2020/0214811 A1 7/2020 Verker et al.
2020/0288981 A1* 9/2020 Li ........................ A61B 5/0066
2021/0045637 A1 2/2021 Chang et al.
2021/0048735 A1* 2/2021 Peckham ............ G03B 21/142

FOREIGN PATENT DOCUMENTS

JP 2005-345937 A 12/2005
JP 2009020424 A * 1/2009
JP 5654583 B2 1/2015
JP 2015-83978 A 4/2015
JP 2016-166765 A 9/2016
JP 6172936 B2 8/2017
KR 10-0595283 B1 7/2006
KR 20060096723 A * 9/2006 .......... H04N 5/7458
KR 10-1533341 B1 7/2015
KR 10-1874547 B1 7/2018
WO 2006/038744 A1 4/2006
WO 2010/145669 A1 12/2010
WO 2021/008686 A1 1/2021

OTHER PUBLICATIONS

Office Action issued Feb. 20, 2024 in Korean Application No. 10-2021-0184287.

* cited by examiner

FIG. 6

HAND-HELD SCANNER

CROSS REFERENCE TO RELATED APPLICATIONS

This application is a National Stage of International Application No. PCT/KR2022/005287 filed on Apr. 12, 2022, claiming priority based on Korean Patent Application No. 10-2021-0048819 filed on Apr. 14, 2021 and Korean Patent Application No. 10-2021-0184287 filed on Dec. 21, 2021.

TECHNICAL FIELD

The present disclosure relates to a hand-held scanner, and more particularly, to an optical engine of the hand-held scanner.

BACKGROUND ART

When a user scans an object by using an oral-cavity scanner, the user has to grip the oral-cavity scanner for a relatively long time, and thus, a structure, a size, and a weight of the oral-cavity scanner may be included in main specification.

The oral-cavity scanner may use a spatial light modulator to project at least two patterns. The spatial light modulator may be divided into a transmissive type and a reflection type. While the reflection type has high efficiency and contrast, compared to the transmissive type, a volume and form of an optical engine thereof may be limited due to a light path.

Therefore, there is a need to develop an oral-cavity scanner to which high degree of freedom in a form factor is applied.

DISCLOSURE

Technical Problem

Provided is a hand-held scanner having a structure for easy grip by a user.

Provided is a hand-held scanner that is easily carried and gripped, by weight-lightening an inner structure of an optical engine of the hand-held scanner.

An oral-cavity scanner provides a high pattern definition by blocking stray light, thereby highly enhancing a quality/definition of an obtained image.

Technical Solution

An embodiment provides a hand-held scanner including: a body in a longitudinal direction; and an optical engine provided in the body and configured to output light, wherein the optical engine includes: a lighting unit configured to emit, along a first axis, light generated from at least one light source; and a projection unit configured to project light emitted from the lighting unit, along a second axis being parallel to the first axis, and wherein directions of the first axis and the second axis are equal.

According to an embodiment, the lighting unit may include a plurality of light sources, a first light source among the plurality of light sources may be provided on the first axis, and light sources excluding the first light source among the plurality of light sources may be provided in a space generated between the first axis and the second axis.

According to an embodiment, the lighting unit may include: a plurality of light sources including a first light source configured to emit first light, a second light source configured to emit second light, and a third light source configured to emit third light; a first filter configured to change a path of the second light to the first axis by passing the first light and reflecting the second light; and a second filter configured to change a path of the third light to the first axis by passing the first light and the second light and reflecting the third light.

According to an embodiment, the lighting unit further may include: a light equalizing unit configured to allow light generated from the at least one light source to have a uniform distribution on a surface to which the light is emitted; and a relay unit configured to relay light output from the light equalizing unit to a prism unit.

According to an embodiment, the relay unit may include a relay lens and a mirror which are configured to focus light output from the light equalizing unit to a light modulator, the relay lens may be perpendicular to an optical axis, and the mirror may be provided with a preset angle with respect to the first axis.

According to an embodiment, the relay lens may be provided in plural, and at least one of the relay lens may be a negative lens.

According to an embodiment, the preset angle may be in a range between 30 degrees and 60 degrees.

According to an embodiment, the prism unit may include: a first prism via which an angle of light received from the lighting unit is changed and relayed to a light modulator; and a second prism via which light received from the first prism is relayed to the light modulator, and light reflected from the light modulator is relayed to the projection unit.

According to an embodiment, the first prism may include a vertex angle with a preset angle.

According to an embodiment, the preset angle may be in a range between 10 degrees and 25 degrees.

According to an embodiment, a refracting angle with respect to a first region including the vertex angle of the first prism may be different from a refracting angle with respect to a second region not including the first region.

According to an embodiment, a material capable of absorbing the light may be coated on a region of the first prism which includes the vertex angle.

According to an embodiment, the optical engine may further include a light modulator including a digital micromirror device (DMD) configured to generate reflected light by reflecting the light being incident with a preset angle via the prism unit.

According to an embodiment, the hand-held scanner may further include a reflective member configured to reflect and emit transmitted light to an object, the transmitted light being transmitted along the second axis, and an optical axis of the reflective member may be perpendicular to the second axis.

According to an embodiment, the hand-held scanner may further include a tip case that can be inserted into and withdrawn from an oral cavity, and the tip case may have an opening being open in a preset direction, and the reflective member being adjacent to the opening.

Advantageous Effects

A hand-held scanner having a structure for easy grip by a user may be provided.

A hand-held scanner that is easily carried and gripped, by weight-lightening an inner structure of an optical engine of the hand-held scanner, may be provided.

An oral-cavity scanner provides a high pattern definition by blocking stray light, so that a quality/definition of an obtained image may be highly enhanced and provided.

DESCRIPTION OF DRAWINGS

The present disclosure will now be described more fully through the detailed descriptions below with reference to the accompanying drawings, in which reference numerals denote structural elements.

FIG. 6 is a diagram for describing a relation between an optical axis of a projection unit and an optical axis of a reflective member, according to an embodiment.

MODE FOR INVENTION

Hereinafter, various embodiments will now be described more fully with reference to the accompanying drawings. The embodiments to be described below may be embodied in many different forms. In order to further clearly describe characteristics of the embodiments, descriptions of features well known to one of ordinary skill in the art to which the embodiments belong are omitted.

Throughout the specification, it will also be understood that when a configuration is referred to as being "connected to" or "coupled with" another configuration, it can be "directly connected to or coupled with" the other configuration, or it can be "connected to or coupled with the other configuration by having an intervening configuration interposed therebetween". Also, when a configuration "includes" or "comprises" another configuration, unless there is a particular description contrary thereto, the configuration can further include other configuration, not excluding the other configuration.

Throughout the specification, it will be understood that, although the terms "first", "second", etc. may be used herein to describe various elements, these elements should not be limited by these terms. These terms are only used to distinguish one element from another element.

Throughout the specification, a "hand-held scanner" may indicate a device configured to obtain image data related to an object. The hand-held scanner may indicate a scanner configured to obtain image data related to an oral cavity which is used in treatment for the oral-cavity. For example, the hand-held scanner may be a scanner that can be inserted into an oral cavity. Here, the hand-held scanner may have a form that can be gripped and carried by one hand.

An "object" is an object to be photographed and may include a human, an animal, or a part thereof. For example, the object may include a body part (such as an organ, etc.), or an artificial structure or a phantom which can be attached onto the object or inserted into the object. For example, the object may include teeth, gingival, at least some regions of an oral cavity, and/or an artificial structure that can be inserted into the oral cavity (e.g., orthodontic devices including brackets and wires, dental repairs including implants, artificial teeth, inlay and onlay, etc., orthodontic aids inserted into the oral cavity, etc.), and teeth or gingival devices with an artificial structure attached thereto. Also, the object may include an impression cast/plaster cast, or the like.

Figure 1:
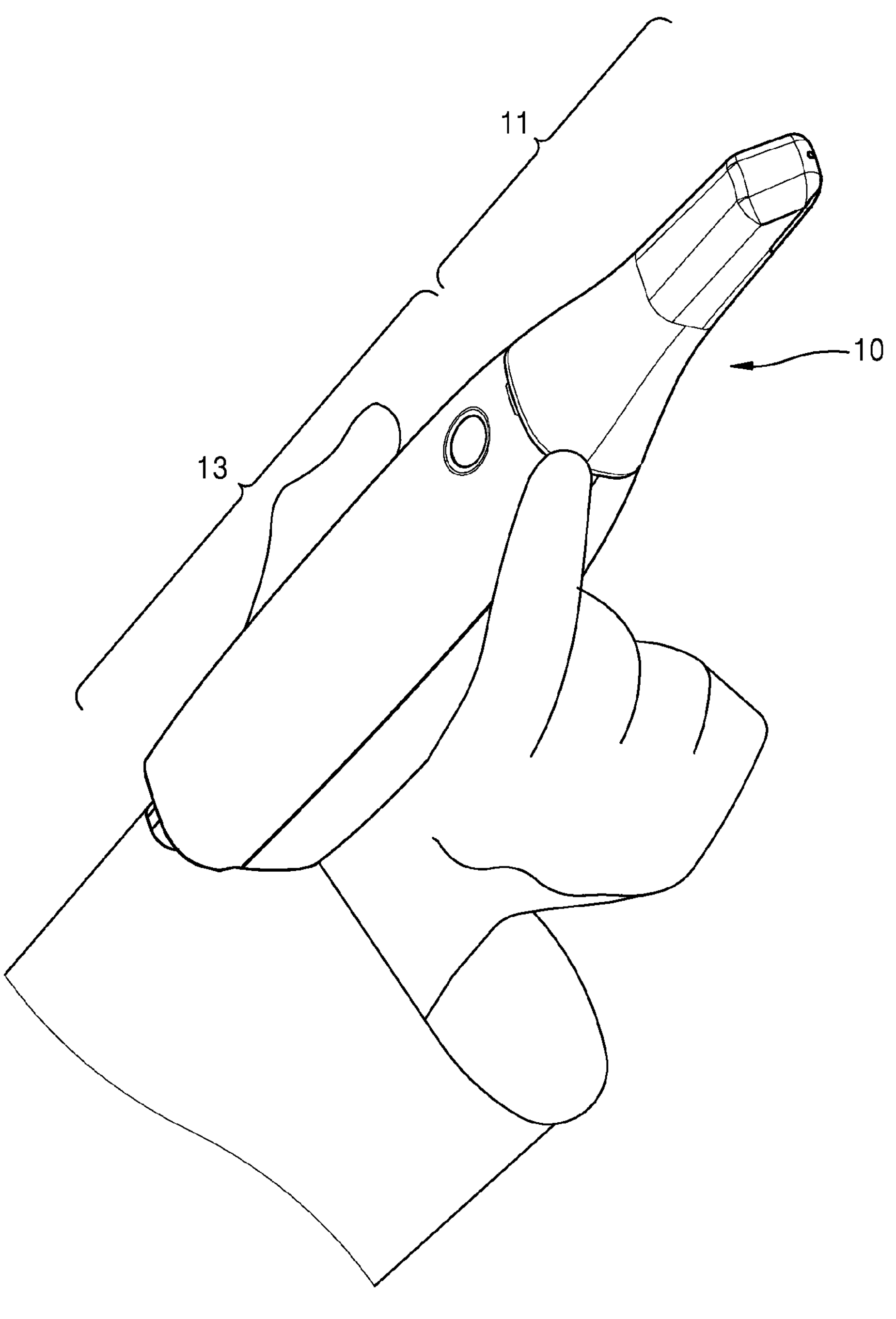
FIG. 1 is a diagram for describing an exterior of a hand-held scanner, according to an embodiment.

FIG. 1 is a diagram for describing an exterior of a hand-held scanner 10, according to an embodiment.

The hand-held scanner 10 shown in FIG. 1 has a pen-type form. The hand-held scanner 10 may include a case 11 that can be inserted into and withdrawn from an oral cavity, and a body 13 that includes configurations for scanning the oral cavity.

As illustrated in FIG. 1, a user may hold the hand-held scanner 10 by gripping the hand-held scanner 10 with a thumb and a forefinger. In this case, when the user grips the hand-held scanner 10 for a long time, a load may be applied to a wrist, and fatigue may increase. Therefore, there is a need to design the hand-held scanner 10 to be compact while allowing a user to easily grip the hand-held scanner 10.

In detail, in the hand-held scanner 10, when a longitudinal direction of the body is long or a height direction thereof is high, it may not be easy for a user to grip the hand-held scanner 10. Therefore, by weight-lightening an inner structure of the hand-held scanner 10, the hand-held scanner 10 that can be easily carried and gripped may be provided.

Figure 2A:
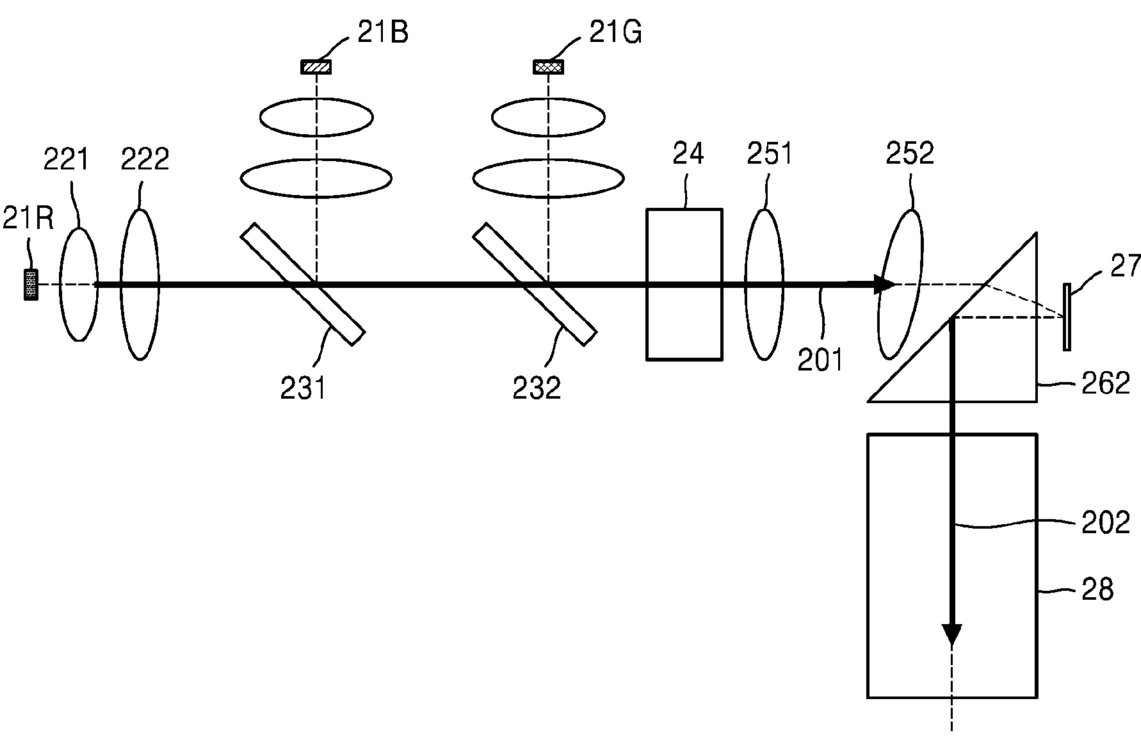
FIGS. 2A and 2B are diagrams for describing an inner structure of an optical engine used in an oral cavity scanner and other technical fields, according to an embodiment.
Figure 2B:
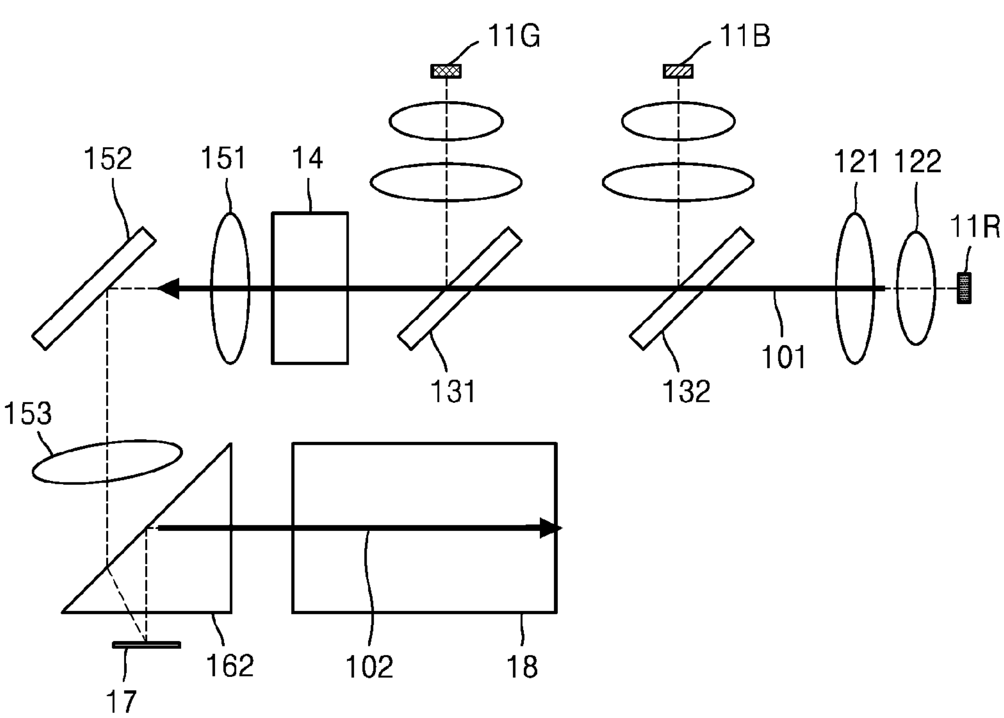

FIGS. 2A and 2B are diagrams for describing an inner structure of an optical engine used in a hand-held scanner and other technical fields, according to an embodiment.

Referring to FIG. 2A, the optical engine may include a plurality of light sources 21R, 21G, and 21B, a plurality of lenses 221 and 222, a plurality of filters 231 and 232, a light equalizing unit 24, relay units 251 and 252, a prism unit 262, a light modulator 27, and a projection unit 28. However, not all elements shown in FIG. 2A are necessary elements of the optical engine. The optical engine may be embodied with more elements than the elements shown in FIG. 2A or may be embodied with less elements than the shown elements.

As illustrated in FIG. 2A, light output from the plurality of light sources 21R, 21G, and 21B may be emitted along a lighting axis 201 and a projection axis 202. Here, the lighting axis 201 and the projection axis 202 may be perpendicular to each other.

When the inner structure of the optical engine shown in FIG. 2A is applied to the hand-held scanner 10, as the lighting axis 201 and the projection axis 202 are perpendicular to each other, it is difficult to realize a pen-type form and compactness. Therefore, when the inner structure of the optical engine shown in FIG. 2A is applied to the hand-held scanner 10, it may not be easy for a user to carry and grip the hand-held scanner 10.

Referring to FIG. 2B, an optical engine may include a plurality of light sources 11R, 11G, and 11B, a plurality of lenses 121 and 122, a plurality of filters 131 and 132, a light equalizing unit 14, relay units 151, 152, and 153, a prism unit 162, a light modulator 17, and a projection unit 18. However, not all elements shown in FIG. 2B are necessary elements of the optical engine. The optical engine may be embodied with more elements than the elements shown in FIG. 2B or may be embodied with less elements than the shown elements.

As illustrated in FIG. 2B, light output from the plurality of light sources 11R, 11G, and 11B may be emitted along a lighting axis 101 and a projection axis 102. Here, the lighting axis 101 and the projection axis 102 may be parallel to each other. The relay unit 152 may be a mirror or a prism, and may bend a path of light along the lighting axis 101 in a direction of the projection axis 102 may.

When the inner structure of the optical engine shown in FIG. 2B is applied to the hand-held scanner 10, as the lighting axis 101 and the projection axis 102 in the hand-held scanner 10 are parallel, it is possible to realize a pen-type form and compactness, compared to the case of FIG. 2A in which the inner structure of the optical engine shown is applied to the hand-held scanner 10. However, as directions of the lighting axis 101 and the projection axis 102 are opposite and it is difficult to ensure a space for the light sources 11G and 11B between the lighting axis and the projection axis, and thus, light sources are provided above the lighting axis 101, such that a height of the optical engine increases, and it may not be easy for a user to grip the hand-held scanner 10.

Therefore, there is a need to design a structure of the hand-held scanner 10 which allows a user to easily carry and grip. For example, by providing a light source in a space generated between a lighting unit and a projection unit due to structures of a relay unit and a prism unit, an optical engine may be weight-lightened. With the reference to FIGS. 3A to 6, a hand-held scanner 10 that can be easily gripped by a user and of which inner structure is weight-lightened will now be described.

Figure 3A:
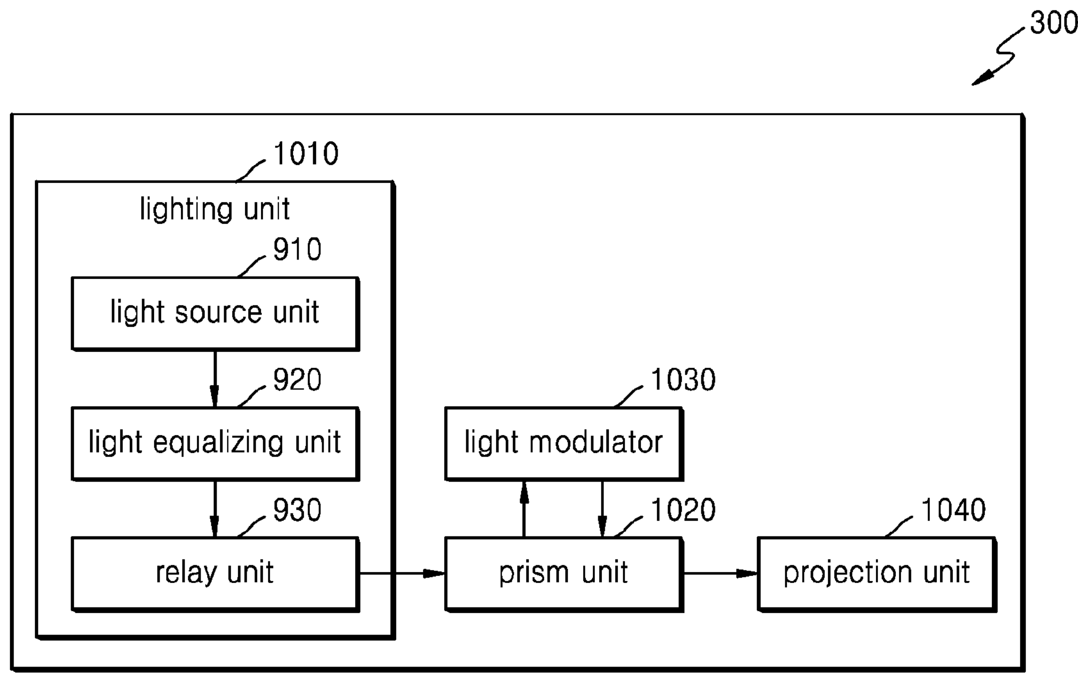
FIG. 3A is a block diagram illustrating a configuration of an optical engine of a hand-held scanner, according to an embodiment.

FIG. 3A is a block diagram illustrating a configuration of an optical engine 300 of the hand-held scanner 10, according to an embodiment.

Referring to FIG. 3A, the optical engine 300 of the hand-held scanner 10 may include a lighting unit 1010, a prism unit 1020, a light modulator 1030, and a projection unit 1040. Also, the lighting unit 1010 may include a light source unit 910, a light equalizing unit 920, and a relay unit 930. However, not all elements shown in FIG. 3A are necessary elements of the optical engine 300. The optical engine 300 may be embodied with more elements than the elements shown in FIG. 3A or the optical engine 300 may be embodied with less elements than the shown elements. Hereinafter, the elements will now be described.

The hand-held scanner 10 may include the optical engine 300 in a body in a longitudinal direction, and the optical engine 300 may output light.

For example, the optical engine 300 may include the lighting unit 1010, the prism unit 1020, and the projection unit 1040. For example, the lighting unit 1010 may emit light along a first axis, the light being generated from at least one light source. The first axis may indicate a lighting axis. The prism unit 1020 may receive light from the lighting unit 1010, and may change a path of the light. The projection unit 1040 may project reflective light generated based on the changed path, along a second axis being parallel to the first axis. The second axis may indicate a projection axis.

For example, the lighting unit 1010 may include the light source unit 910. For example, the light source unit 910 may include a plurality of light sources. A first light source among the plurality of light sources may be provided on the first axis, and light sources excluding the first light source among the plurality of light sources may be provided in a space generated between the first axis and the second axis. The first axis and the second axis may be parallel to each other and directions of the first axis and the second axis may be same directions. Due to a locational relation of the first axis and the second axis, a space may be generated between the lighting unit 1010 and the projection unit 1040. As a light source is provided in a space generated between the lighting unit 1010 and the projection unit 1040, it is possible to prevent an increase in a height of the optical engine 300. A structure in which a plurality of light sources are provided will be described with reference to FIG. 3B.

For example, the light sources excluding the first light source among the plurality of light sources may be a second light source and a third light source. The second light source and the third light source may be provided in such a manner that emission directions of a second light emitted from the second light source and a third light emitted from the third light source may be parallel to each other. By providing the second light source and the third light source in a parallel manner, space usability may be increased.

For example, the lighting unit 1010 may include a plurality of light sources including a first light source to emit first light, a second light source to emit second light, and a third light source to emit third light, a first filter to change a path of the second light to a first axis by passing the first light and reflecting the second light, and a second filter to change a path of the third light to the first axis by passing the first light and the second light and reflecting the third light.

For example, the light source unit 910 may include a light source. For example, the light source may be a light emitting diode (LED), a lamp, or a laser. Compared to the LED, the laser may have high efficiency due to its small emission angle, but may cause image defect due to a speckle. Also, the LED easily ensures uniform light, due to a Lambertian characteristic of an equal amount of light in all directions, has a small volume, and thus, may be used as the light source of the light source unit 910.

For example, the first light source may be an LED that emits red light, the second light source may be an LED that emits blue light, and the third light source may be an LED that emits green light.

For example, the lighting unit 1010 may include the light equalizing unit 920 to allow light generated from at least one light source to have a uniform distribution on a surface to which the light is emitted.

For example, the lighting unit 1010 may include the relay unit 930 to relay light output from the light equalizing unit 920 to the prism unit 1020. The relay unit 930 may include a relay lens and a mirror which are configured to focus the light output from the light equalizing unit 920 to the light modulator 1030. The relay lens may be perpendicular to an optical axis. For example, at least two of relay lenses may be provided. Also, the mirror may be provided with a preset angle with respect to the first axis.

For example, the prism unit 1020 may include a first prism via which an angle of light received from the relay unit 930 is changed and relayed to the light modulator 1030, and a second prism via which light received from the first prism is relayed to the light modulator 1030 and light reflected from the light modulator 1030 is relayed to the projection unit 1040.

For example, the first prism may have a vertex angle with a preset angle. For example, the preset angle may be in range between 10 degrees and 25 degrees. As the first prism is provided with the preset angle, a height of the optical engine may be decreased, and uniformity of light-emission may be enhanced.

For example, a refracting angle with respect to a first region including the vertex angle of the first prism may be different from a refracting angle with respect to a second region not including the first region.

For example, the hand-held scanner 10 may further include the light modulator 1030 including a digital micro-mirror device (DMD) for generating pattern light by reflecting light being incident with a preset angle via the prism unit 1020.

For example, the hand-held scanner 10 may further include a reflective member to reflect and emit projected light to an object, the projected light being projected along the second axis. For example, a center axis of the reflective member may be aligned with the second axis, and an optical axis of the reflective member may be perpendicular to the second axis.

For example, the hand-held scanner 10 may further include a tip case that can be inserted into and withdrawn from an oral cavity. The tip case may have an opening being open in a preset direction, and a reflective member being adjacent to the opening. For example, the reflective member may be a mirror, and may change a path of light projected by the projection unit 1040 so as to emit the projected light to an object.

Figure 3B:
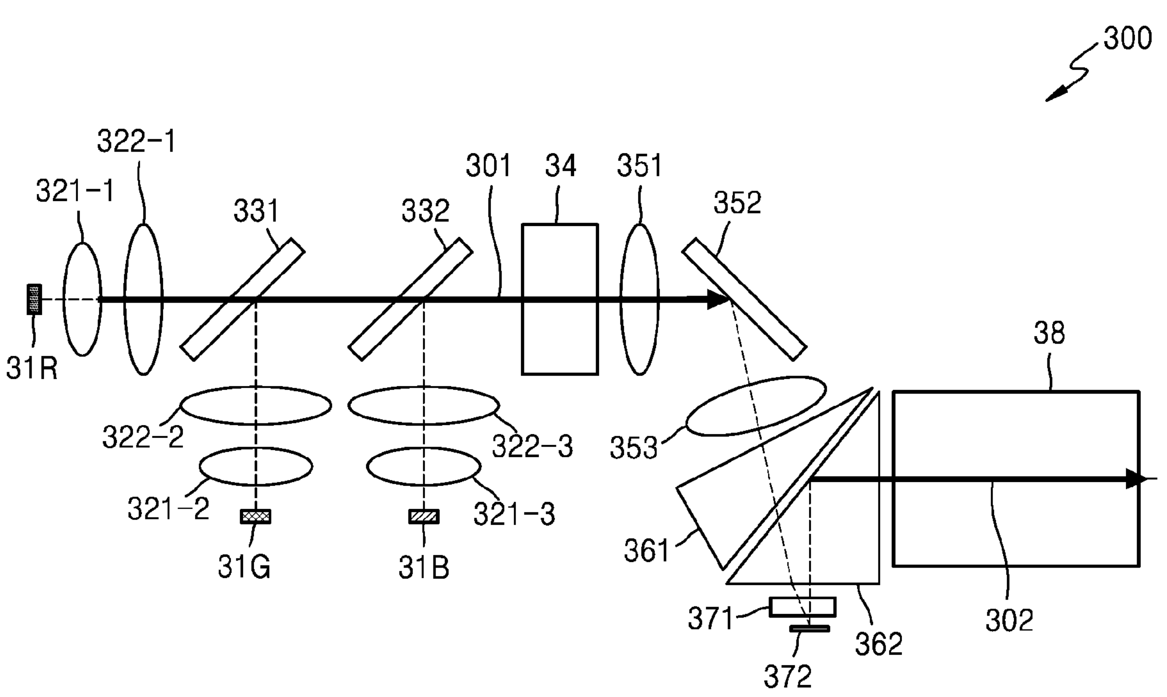
FIG. 3B is a diagram for describing an inner structure of the optical engine described with reference to FIG. 3A.

FIG. 3B is a diagram for describing an inner structure of the optical engine 300 described with reference to FIG. 3A.

The light source unit 910 described with reference to FIG. 3A may correspond to a light source unit to be described with reference to FIG. 3B, the light equalizing unit 920 described with reference to FIG. 3A may correspond to a light equalizing unit 34 to be described with reference to FIG. 3B, the relay unit 930 described with reference to FIG. 3A may correspond to relay units 351, 352, and 353 to be described with reference to FIG. 3B, the prism unit 1020 described with reference to FIG. 3A may correspond to prism units 361 and 362 to be described with reference to FIG. 3B, the light modulator 1030 described with reference to FIG. 3A may correspond to light modulators 371 and 372 to be described with reference to FIG. 3B, and the projection unit 1040 described with reference to FIG. 3A may correspond to a projection unit 38.

A lighting unit of the optical engine may include a light source unit, a light equalizing unit, and a relay unit. Referring to FIG. 3B, the light source unit may include a plurality of light sources 31R, 31G, and 31B, a plurality of lenses 321-1, 322-1, 321-2, 322-2, 321-3, and 322-3, and a plurality of filters 331 and 332.

For example, the plurality of light sources 31R, 31G, and 31B may include a first light source 31R for emitting first light, a second light source 31G for emitting second light, and a third light source 31B for emitting third light. For example, the first light source 31R may be an LED to emit red light, the second light source 31G may be an LED to emit green light, and the third light source 31B may be an LED to emit blue light. The present disclosure is not limited to an embodiment in which the light source unit of the hand-held scanner includes a plurality of light sources.

Also, the plurality of lenses 321-1, 322-1, 321-2, 322-2, 321-3, and 322-3 may collimate light emitted from the plurality of light sources 31R, 31G, and 31B. In detail, light emitted from the first light source 31R may be collimated due to the lenses 321-1 and 322-1, light emitted from the second light source 31G may be collimated due to the lenses 321-2 and 322-2, and light emitted from the third light source 31B may be collimated due to the lenses 321-3 and 322-3. Also, the plurality of lenses 321-1, 322-1, 321-2, 322-2, 321-3, and 322-3 may be referred to as collimator lenses.

For example, the plurality of lenses 321-1, 321-2, and 321-3 may be glass lenses with both convex surfaces having a positive power. Also, the plurality of lenses 322-1, 322-2, and 322-3 may be plastic lenses with aspherical surfaces having a positive power.

Also, each of the plurality of filters 331 and 332 may include a coated surface for reflecting preset light and a surface for transmitting light different from the preset light. For example, the first filter 331 may include a surface for transmitting first light and a coated surface for reflecting second light. The first filter 331 may transmit first light and reflect second light, thereby changing a path of the second light to a first axis 301. For example, the second filter 332 may include a surface for transmitting first light and second light, and a coated surface for reflecting third light. The second filter 332 may transmit the first light and the second light, and reflect the third light, thereby changing a path of the third light to the first axis 301. Also, the plurality of filters 331 and 332 may be dichroic filters. Lights respectively emitted from the plurality of light sources 31R, 31G, and 31B may be synthesized by the plurality of filters 331 and 332.

The light equalizing unit 34 may uniformize light by compensating for distortion of the synthesized light. In general, as light emitted from a light source has a bright center and dim edges, the light equalizing unit 34 may compensate for distortion so as to allow lights emitted from the plurality of light sources 31R, 31G, and 31B to have a uniform distribution.

For example, the light equalizing unit 34 may emit light within a particular angle so as to allow the light to have a uniform distribution in luminance. That is, the light equalizing unit 34 may serve as second lighting having a uniform emission angle.

For example, the light equalizing unit 34 may include a light guide in the form of glass rod. For example, light incident on one flat surface of the glass rod may proceed to the other surface of the glass rod due to inner total reflection.

For example, the light equalizing unit 34 may include a micro-lens array. The micro-lens array has a form in which lenses with a micro-meter size are arrayed, and may be advantageous in minimization of the optical engine. According to setting of uniformity and size, the number of arrays may be adjusted.

For example, the light equalizing unit 34 may include a fly eye lens in which a plurality of lenses whose both curved surfaces have the same aspherical curvature are two-dimensionally arrayed.

Light that is transmitted via the light equalizing unit 34 may be focused with a random angle to the light modulators 371 and 372 via the relay units 351, 352, and 353 and the prism units 361 and 362. The relay units 351, 352, and 353 may include a plurality of lenses for collimating light from the light equalizing unit 34 and transferring the light to the prism units 361 and 362. The relay units 351, 352, and 353 may collect emitted light with an appropriate size so as to allow the light emitted from the light equalizing unit 34 to be positioned on the light modulators 371 and 372.

For example, the relay units 351 and 353 may be configured as lenses having a positive (+) refractive power to focus light to match sizes of the light modulators 371 and 372. For example, as the optical engine becomes small, a relay path becomes short, and thus, lenses have to be arrayed in a small space. Therefore, by using aspherical lenses as lenses of the relay units 351 and 353, a small number of lenses may be used in a small space while light-focusing efficiency is increased. For example, the relay units 351 and 353 may be perpendicular to an optical axis.

For example, in order to decrease a height of the optical engine 300, the relay unit 352 may be slanted within a preset range of an acute angle with respect to a first axis 301. As it is necessary to increase a path of light from the light equalizing unit 34 to the light modulators 371 and 372 and to ensure a space for the relay unit 352, the relay unit 351 may be a glass lens having a negative power, and the relay unit 353 may be a plastic lens with an aspherical surface having a positive power. That is, for minimization of the optical engine 300, the relay unit 353 may be provided as shown in FIG. 3, the relay unit 351 may be a glass lens having a negative power, and the relay unit 353 may be a plastic lens with an aspherical surface having a positive power.

The prism units 361 and 362 may receive light from the lighting unit and may change a path of the light. For example, the prism units 361 and 362 may change a path of light so as to focus the light on the light modulators 371 and 372 with a random angle. In detail, the prism units 361 and 362 may include a first prism 361 for changing an angle of light received from the lighting unit and transferring the light to the light modulators 371 and 372, and a second prism 362 for transferring light received from the first prism 361 to the light modulators 371 and 372, and transferring light reflected from the light modulators 371 and 372 to the projection unit 38. The second prism 362 may separate incident light being incident to the light modulators 371 and 372 from reflected light reflected from the light modulators 371 and 372, according to operations of the light modulators 371 and 372.

When light output from the lighting unit is incident with a random angle via the prism units 361 and 362, the light modulators 371 and 372 may generate reflected light by reflecting the incident light. For example, the light modulators 371 and 372 may consist of a glass film 371 and a panel 372.

For example, the panel 372 may include a DMD, micro electro mechanical systems (MEMS), or the like to generate a pattern of light. For example, the panel 372 including a DMD includes a plurality of mirrors and turns on or off each mirror, according to a control signal, thereby controlling light incident on the panel 372, in a pixel unit corresponding to each mirror. Also, the glass film 371 may protect the panel 372. The glass film 371 may be provided outside the light modulator 372.

For example, light reflected from an on-state mirror from among lights incident on the DMD may be totally reflected from a surface of the second prism 362 and then may be transferred to the projection unit 38. As the DMD does not have a liquid crystal display (LCD) panel, there is no a polarization loss. Also, as the DMD individually controls a micro-mirror, a high definition may be obtained without a color diffusion.

Reflected light reflected from the light modulators 371 and 372 may be transferred to the second prism 362, and reflected light totally reflected from the second prism 362 may be transmitted along a second axis 302 of the projection unit 38. The projection unit 38 may magnify or reduce light reflected from or transmitted by the light modulators 371 and 372, according to a rate, and thus, may project the light onto an object.

Figure 4:
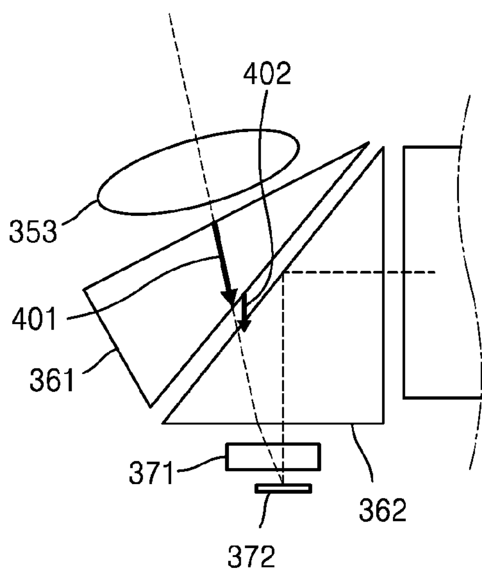
FIG. 4 is a diagram for describing a structure and operation of a prism unit and a light modulator, according to an embodiment.

FIG. 4 is a diagram for describing in detail a structure and operation of a prism unit and a light modulator, according to an embodiment.

FIG. 4 illustrates the relay units 351, 352, and 353, the prism units 361 and 362, and the light modulators 371 and 372 in the structure of the optical engine 300 shown in FIG. 3B.

The first prism 361 may decrease a height of the optical engine by partially bending an angle of light received from the relay units 353. Also, as the height of the optical engine is decreased, a grip feeling with respect to a pen-type hand-held scanner may be enhanced.

For example, without the first prism 361, an angle of light corresponds to a direction 402, such that the height of the optical engine is increased. Therefore, as the first prism 361 is provided in the optical engine, an angle of light is bent to an angle corresponding to a direction 401, and thus, the height of the optical engine may be decreased.

For example, a range of a vertex angle of the first prism 361 may be designed to be between 10 degrees and 25 degrees. When an angle of the vertex angle of the first prism 361 is further increased, a difference in a path of light increases such that optical efficiency and uniformity may deteriorate, and thus, the first prism 361 may be provided within the range.

When the relay unit 353 is slanted, optical efficiency may increase but a difference in a path of light increases, such that uniformity may be decreased. Therefore, as shown in FIG. 4, the relay unit 353 is not slanted but the first prism 361 having a preset vertex angle is used, such that the height of the optical engine may be decreased, and optical efficiency and appropriate uniformity may be ensured. That the relay unit 353 is not slanted may indicate that the relay unit 353 is provided such that a plane of the relay unit 353 is perpendicular to an incident light. According to the structure of the optical engine 300 shown in FIG. 4, the minimized hand-held scanner 10 may be provided.

Also, the relay unit 352 shown in FIG. 3 may be a mirror, and the mirror may be provided in a range between 30 degrees and 60 degrees in a clockwise direction with respect to the first axis 301. By providing the mirror with an angle within a preset range, a lighting beam may be incident with an appropriate slant on the first prism, such that the height of the optical engine may be decreased and uniformity may be enhanced.

Figure 5A:
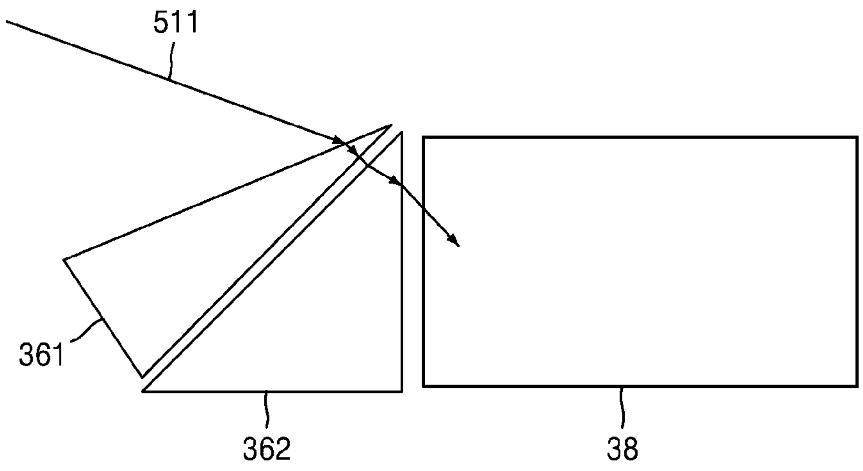
FIG. 5A is a diagram for describing a case in which stray light is incident on a projection unit.

FIG. 5A is a diagram for describing a case in which stray light is incident on a projection unit.

Referring to FIGS. 3A and 5A, as the first axis 301 of the lighting unit and the second axis 302 of the projection unit are parallel to each other, light 511 slantly incident on the first prism 361 may directly enter the projection unit 38 via the second prism 362. When stray light that enters the projection unit 38 occurs, light may output from a location of a pixel turned off by a DMD, and a projected pattern is not clear, such that a quality or definition of an obtained image may deteriorate. Therefore, there is a need for the design capable of blocking stray light entering the projection unit 38.

Figure 5B:
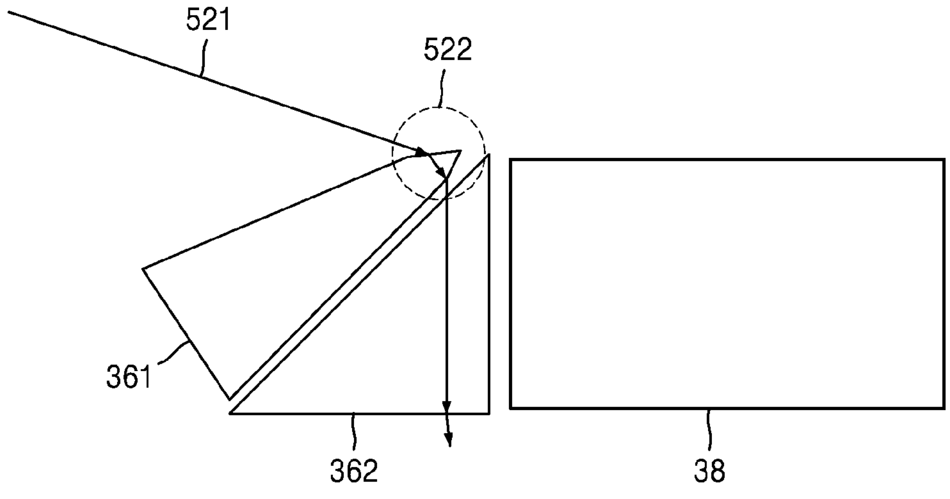
FIGS. 5B and 5C are diagrams for describing prism units for blocking stray light from entering a projection unit, according to an embodiment.
Figure 5C:
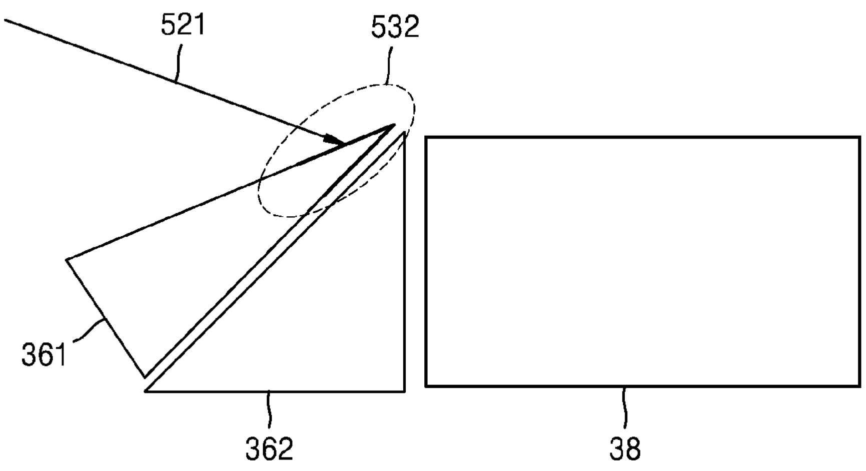

FIGS. 5B and 5C are diagrams for describing prism units for blocking stray light from entering a projection unit, according to an embodiment.

Referring to FIG. 5B, the first prism 361 may be designed in such a manner that a refractive index of a first region 522 including a vertex angle of the first prism 361 is different from a refractive index of a second region not including the first region 522. Here, the second region may be a region of the first prism 361 which excludes the first region 522.

For example, in the first prism 361, a form of a vertex angle of the first prism 361 shown in FIG. 5A may be designed and modified to a form of a vertex angle of the first prism 361 shown in FIG. 5B. A refractive index with respect to a peripheral region of the vertex angle of the first prism 361 shown in FIG. 5B may be different from a refractive index with respect to a peripheral region of the vertex angle of the first prism 361 shown in FIG. 5A. Here, a refractive index of a region not including a vertex angle is equal to the refractive index with respect to the peripheral region of the vertex angle of the first prism 361 shown in FIG. 5A. Therefore, light 521 that is slantly incident on the first prism 361 may not enter the projection unit 38 but may be emitted to the second prism 362.

Alternatively, referring to FIG. 5C, a material capable of absorbing light (for example: black-color pigment) may be coated on a region 532 of the first prism 361 which includes the vertex angle of the first prism 361. For example, the material capable of absorbing light may be coated from a tip of the vertex angle to a preset point of a corner thereof. Therefore, light 521 that is slantly incident on the first prism 361 is absorbed by the material capable of absorbing light, and thus, does not enter the first prism 361, the second prism 362, and the projection unit 38.

Figure 6:
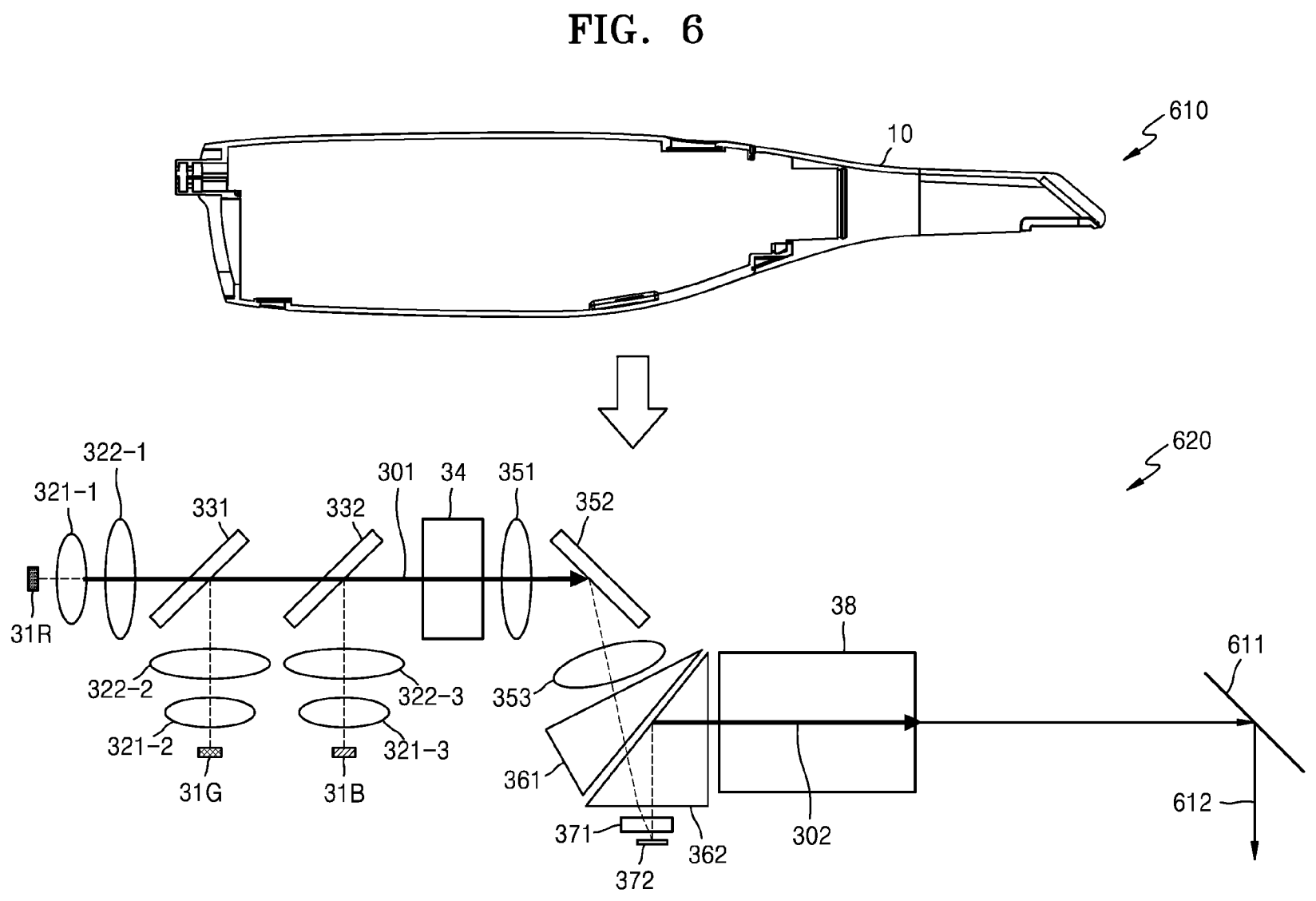

FIG. 6 is a diagram for describing a relation between an optical axis of a projection unit and an optical axis of a reflective member, according to an embodiment.

An image 610 of FIG. 6 shows an exterior of a hand-held scanner. An image 620 of FIG. 6 shows an inner structure of an optical engine of the hand-held scanner.

Configurations of the plurality of light sources 31R, 31G, and 31B, the plurality of lenses 321-1, 322-1, 321-2, 322-2, 321-3, and 322-3, and the plurality of filters 331 and 332, the light equalizing unit 34, the relay units 351, 352, and 353, the prism units 361 and 362, the light modulators 371 and 372, and the projection unit 38, which are shown in the image 620 of FIG. 6, are the same as configurations shown in FIG. 3B. Thus, redundant descriptions are omitted.

For example, the hand-held scanner may further include a reflective member 611 to reflect and emit transmitted light to an object, the transmitted light being transmitted along the second axis 302. Here, an optical axis 612 of the reflective member 611 may be perpendicular to the second axis 302.

For example, the reflective member 611 may be a mirror or a prism. The reflective member 611 may emit the transmitted light to the object by reflecting the transmitted light in a perpendicular manner to the second axis 302. As the optical axis 612 of the reflective member 611 is perpendicular to the second axis 302, light may be easily emitted on the object.

A hand-held scanner described in the present disclosure may be implemented using hardware elements, software elements, and/or a combination of hardware and software elements. Also, a computer program stored in a computer-readable recording medium so as to perform an operating method of the hand-held scanner may be provided. The embodiments of the present disclosure may be written into a program that may be executed by a computer, and may be implemented in a universal digital computer for carrying out the program by using a computer-readable recording medium.

While the embodiments have been particularly shown and described in detail, it will be understood by one of ordinary skill in the art that various changes in form and details may be made therein without departing from the spirit and scope of the disclosure as defined by the following claims.

The invention claimed is:

1. A hand-held scanner comprising:

a body in a longitudinal direction; and an optical engine provided in the body and configured to output light, wherein the optical engine comprises:

a lighting unit configured to emit, along a first axis, light generated from at least one light source;

a prism unit comprising:

a first prism via which an angle of light incident from the lighting unit through a first surface is changed and the light is transmitted to a second prism through a second surface; and the second prism via which light received from the first prism is transmitted to a light modulator, and light reflected from the light modulator is transmitted to a projection unit, and the projection unit configured to project light transmitted through the second prism, along a second axis being parallel to the first axis, and wherein directions of the first axis and the second axis are equal, wherein the lighting unit further comprises:

a light equalizing unit configured to allow light generated from the at least one light source to have a uniform distribution on a surface to which the light is emitted; and a relay unit configured to relay light output from the light equalizing unit to the prism unit, wherein the relay unit comprises a first relay lens, a mirror and a second relay lens which are configured to focus light output from the light equalizing unit to the light modulator, wherein the mirror is slanted within a preset range of an acute angle with respect to the first axis, and wherein the first relay lens is a lens having a negative refractive power and the second relay lens is a lens with an aspherical surface having a positive refractive power.

2. The hand-held scanner of claim 1, wherein the lighting unit comprises a plurality of light sources, a first light source among the plurality of light sources is provided on the first axis, and light sources excluding the first light source among the plurality of light sources are provided in a space generated between the first axis and the second axis.

3. The hand-held scanner of claim 1, wherein the lighting unit comprises:

a plurality of light sources comprising a first light source configured to emit first light, a second light source configured to emit second light, and a third light source configured to emit third light;

a first filter configured to change a path of the second light to the first axis by passing the first light and reflecting the second light; and a second filter configured to change a path of the third light to the first axis by passing the first light and the second light and reflecting the third light.

4. The hand-held scanner of claim 1, wherein the preset range of an acute angle is a range between 30 degrees and 60 degrees.

5. The hand-held scanner of claim 1, wherein a vertex angle formed by the first surface and the second surface of the first prism has a preset angle.

6. The hand-held scanner of claim 5, wherein the preset angle is in a range between 10 degrees and 25 degrees.

7. The hand-held scanner of claim 5, wherein a refracting angle with respect to a first region comprising the vertex angle of the first prism is different from a refracting angle with respect to a second region not comprising the first region.

8. The hand-held scanner of claim 5, wherein a material capable of absorbing the light is coated on a region of the first prism which comprises the vertex angle.

9. The hand-held scanner of claim 1, wherein the light modulator comprises a digital micro-mirror device (DMD) configured to generate reflected light by reflecting the light received from the first prism.

10. The hand-held scanner of claim 1, wherein the hand-held scanner further comprises a reflective member configured to reflect and emit transmitted light to an object, the transmitted light being transmitted along the second axis, and an optical axis of the reflective member is perpendicular to the second axis.

11. The hand-held scanner of claim 10, wherein the hand-held scanner further comprises a tip case that can be inserted into and withdrawn from an oral cavity, and the tip case has an opening being open in a preset direction, and the reflective member being adjacent to the opening.

* * * * *